United States Patent
Craft

(10) Patent No.: US 11,141,459 B2
(45) Date of Patent: Oct. 12, 2021

(54) PHARMACEUTICAL COMPOSITION COMPRISING LEFTY

(71) Applicant: GRANT LABS, INC., Shepherdstown, WV (US)

(72) Inventor: Charles E. Craft, Shepherdstown, WV (US)

(73) Assignee: GRANT LABS, INC., Shepherdstown, WV (US)

(*) Notice: Subject to any disclaimer, the term of this patent is extended or adjusted under 35 U.S.C. 154(b) by 0 days.

(21) Appl. No.: 16/180,466

(22) Filed: Nov. 5, 2018

(65) Prior Publication Data

US 2019/0070260 A1 Mar. 7, 2019

Related U.S. Application Data

(62) Division of application No. 15/029,829, filed as application No. PCT/US2014/061048 on Oct. 17, 2014, now Pat. No. 10,117,908.

(60) Provisional application No. 61/892,076, filed on Oct. 17, 2013.

(51) Int. Cl.
| | |
|---|---|
| *C07K 14/475* | (2006.01) |
| *C07K 14/495* | (2006.01) |
| *A61K 38/18* | (2006.01) |
| *A61K 8/04* | (2006.01) |
| *A61K 47/10* | (2017.01) |
| *A61K 47/14* | (2017.01) |
| *A61K 47/18* | (2017.01) |
| *A61K 47/22* | (2006.01) |
| *A61K 9/00* | (2006.01) |
| *A61K 47/32* | (2006.01) |
| *A61K 38/17* | (2006.01) |
| *A61K 45/06* | (2006.01) |

(52) U.S. Cl.
CPC .............. *A61K 38/18* (2013.01); *A61K 8/042* (2013.01); *A61K 9/0014* (2013.01); *A61K 38/1709* (2013.01); *A61K 45/06* (2013.01); *A61K 47/10* (2013.01); *A61K 47/14* (2013.01); *A61K 47/18* (2013.01); *A61K 47/22* (2013.01); *A61K 47/32* (2013.01); *C07K 14/475* (2013.01); *C07K 14/495* (2013.01); *A61K 38/1841* (2013.01)

(58) Field of Classification Search
CPC .... A61K 38/18; A61K 38/1841; A61K 8/042; C07K 14/475; C07K 14/495
See application file for complete search history.

(56) References Cited

U.S. PATENT DOCUMENTS

| | | | |
|---|---|---|---|
| 4,179,337 A | 12/1979 | Davis | |
| 5,234,784 A | 8/1993 | Aslam et al. | |
| 6,071,942 A | 6/2000 | Hellstrand et al. | |
| 6,428,966 B1 | 8/2002 | Lee et al. | |
| 6,635,480 B1 | 10/2003 | Lee et al. | |
| 7,612,040 B2* | 11/2009 | Knopf .................... | A61P 25/14 514/1.1 |
| 8,106,004 B2 | 1/2012 | Hendrix et al. | |
| 2002/0086351 A1* | 7/2002 | Ebner ..................... | C07K 14/47 435/69.1 |
| 2007/0078101 A1 | 4/2007 | Brivanlou et al. | |
| 2008/0242604 A1 | 10/2008 | Ebner et al. | |
| 2010/0135904 A1 | 6/2010 | Gray et al. | |
| 2010/0160225 A1 | 6/2010 | Knopf et al. | |
| 2012/0207744 A1 | 8/2012 | Mendlein | |
| 2013/0102541 A1 | 4/2013 | Hendrix et al. | |
| 2016/0279198 A1 | 9/2016 | Hendrix et al. | |

FOREIGN PATENT DOCUMENTS

| | | |
|---|---|---|
| EP | 0154316 B1 | 9/1985 |
| EP | 0401384 B | 3/1996 |
| WO | 2011031875 A2 | 3/2011 |
| WO | 2013064692 A1 | 5/2013 |
| WO | 2015058040 A1 | 4/2015 |

OTHER PUBLICATIONS

Definition of "irrigation" from Merriam-Webster dictionary www.merriam-webster.com/dictionary/irrigation; accessed Mar. 31, 2020.*
Definition of "spray" from Merriam-Webster dictionary www.merriam-webster.com/dictionary/spray; accessed Mar. 31, 2020.*
Kosaki et al. Characterization and mutation analysis of human Lefty A and Lefty B, homologues of murine genes implicated in left-right axis development. Am J Hum Genet 64: 712-721, 1999.*
Kothapalli et al. Detection of ebaf, a novel human gene of the transforming growth factor beta superfamily association of gene expression with endometrial bleeding. J Clin Invest 99(10): 2342-2350, 1997.*
Meno et al. Two closely-related left-right asymmetrically expressed genes, lefty-1 and lefty-2: their distinct expression domains, chromosomal linkage and direct neuralizing activity in Xenopus embryos. Genes Cells 2: 513-524, 1997.*

(Continued)

*Primary Examiner* — Bridget E Bunner

(74) *Attorney, Agent, or Firm* — Casimir Jones, S.C.; David A. Casimir

(57) ABSTRACT

The present disclosure relates to suppression of cellular transformation and dysplasia by topical application of Lefty. In particular, the present disclosure provides compositions and methods for topically applying Lefty to treat and prevent cancers.

8 Claims, No Drawings

(56) References Cited

OTHER PUBLICATIONS

Definition of "emollient" from medical-dictionary.thefreedictionary.com/emollient; accessed on Dec. 21, 2020.*
Bottger et al., "Identification of novel mdm2 binding peptides by phage display." Oncogene. Nov. 21, 1996;13(10):2141-7.
Bottger et al., "Molecular characterization of the hdm2-p53 interaction." J Mol Biol. Jun. 27, 1997;269(5):744-56.
International Search Report of related application No. PCT/US2014/061048, dated Dec. 24, 2014, 15 pages.
Sulochana et al., "Developing antiangiogenic peptide drugs for angiogenesis-related diseases." Curr Pharm Des. 2007;13(20):2074-86.
Erb et al., "Apoptosis and pathogenesis of melanoma and nonmelanoma skin cancer." Adv Exp Med Biol. 2008;624:283-95.
Hendrix et al., "Reprogramming metastatic tumour cells with embryonic microenvironments."Nat Rev Cancer. Apr. 2007;7(4):246-55.
Topczewska et al., "Embryonic and tumorigenic pathways converge via Nodal signaling: role in melanoma aggressiveness" Nat Med. Aug. 2006;12(8):925-32.

* cited by examiner

US 11,141,459 B2

PHARMACEUTICAL COMPOSITION COMPRISING LEFTY

The present application is a divisional of U.S. application Ser. No. 15/029,829, filed Apr. 15, 2016, which is a 371 U.S. National Phase Entry of International Application No. PCT/US2014/061048, filed Oct. 17, 2014, which claims priority to U.S. Patent Application Ser. No. 61/892,076, filed Oct. 17, 2013, the disclosures of which are herein incorporated by reference in their entireties.

FIELD OF THE INVENTION

The present disclosure relates to suppression of cellular transformation and dysplasia by topical application of Lefty. In particular, the present disclosure provides compositions and methods for topically applying Lefty to treat and prevent disease.

BACKGROUND OF THE INVENTION

Melanoma is a malignant tumor of melanocytes. Melanocytes produce the dark pigment, melanin, which is responsible for the color of skin. These cells predominantly occur in skin, but are also found in other parts of the body, including the bowel and the eye (uveal melanoma). Melanoma can originate in any part of the body that contains melanocytes.

Melanoma is less common than other skin cancers. However, it is much more dangerous if it is not found early. It causes the majority (75%) of deaths related to skin cancer. Worldwide, doctors diagnose about 160,000 new cases of melanoma yearly. In women, the most common site is the legs and melanomas in men are most common on the back. It is particularly common among Caucasians, especially northwestern Europeans living in sunny climates. There are high rates of incidence in Oceania, Northern America, Europe, Southern Africa, and Latin America, with a paradoxical decrease in southern Italy and Sicily. This geographic pattern reflects the primary cause, ultraviolet light (UV) exposure crossed with the amount of skin pigmentation in the population.

According to a WHO report, about 48,000 melanoma related deaths occur worldwide per year. The treatment includes surgical removal of the tumor. If melanoma is found early, while it is still small and thin, and if it is completely removed, then the chance of cure is high. The likelihood of the melanoma coming back or spreading depends on how deeply it has gone into the layers of the skin. For melanomas that come back or spread, treatments include chemo- and immunotherapy, or radiation therapy.

Additional methods for treating and preventing melanoma are needed.

SUMMARY OF THE INVENTION

The present disclosure relates to suppression of cellular transformation and dysplasia by topical application of Lefty. In particular, the present disclosure provides compositions and methods for topically applying Lefty to treat and prevent disease.

In some embodiments, the present disclosure provides a pharmaceutical composition for topical administration comprising a Lefty polypeptide. In some embodiments, the Lefty is glycosylated. In some embodiments, the Lefty is recombinant human Lefty or is isolated from human embryonic stem cells. In some embodiments, the composition comprises histamine. In some embodiments, the composition comprises one or more additional components (e.g., ethanol, trolamine, carbomer, methyl paraben, propyl paraben, or PBS). In some embodiments, Lefty is present in said composition as a concentration of between 1 ng/ml and 1000 ng/ml (e.g., between 10 and 500 ng/ml).

The present disclosure further provides a method of treating or preventing a disease on a surface of the body of a subject, comprising contacting the surface with any one of the topical Lefty compositions described herein. In some embodiments, the disease is cancer, for example, a skin cancer (e.g., basal cell carcinoma, squamous cell carcinoma, or malignant melanoma). In some embodiments, the surface is, for example, a nevi, a site comprising a pre-cancerous lesion, a tissue of ectodermal origin (e.g., epidermis, mucosal surfaces, cornea, neural crest origin tissue, melanocytes, or retina), the site of removal of a cancerous or precancerous lesion, or a site suspected of comprising a cancerous or pre-cancerous lesion. In some embodiments, the contacting treats cancer or prevents a pre-cancerous lesion from becoming cancerous. In some embodiments, the contacting is performed continuously over a period of weeks or months (e.g., one or more times a day for a period of days, weeks, months, or years).

In some embodiments, the method further comprises the step of administering a known chemotherapy agent. In some embodiments, the known chemotherapy agent is administered concurrently or sequentially with the topical Lefty composition. For example, in some embodiments, the known chemotherapeutic agent is administered prior to or following the topical Lefty composition. In some embodiments, there is gap of several days (e.g., 1, 2, 3, 4, 5, 6, 7, 8, 9, 10 or more days) between the administration of the topical Lefty composition and the administration of the known chemotherapeutic agent.

Additional embodiments will be apparent to persons skilled in the relevant art based on the teachings contained herein.

Definitions

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "purified" or "to purify" refers to the removal of components (e.g., contaminants) from a sample. For example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION OF THE INVENTION

The present disclosure relates to suppression of cellular transformation and dysplasia by topical application of Lefty. In particular, the present disclosure provides compositions and methods for topically applying Lefty to treat and prevent diseases associated with cellular transformation or dysplasia.

I. Pharmaceutical Compositions Comprising Lefty

Embodiments of the present disclosure provide compositions and methods for topical application of Lefty. The present disclosure is not limited to particular Lefty polypeptides or topical formulations. Exemplary Lefty polypeptides and formulations are described herein.

A. Lefty Polypeptides

The present disclosure is not limited to a particular Lefty polypeptide. Exemplary Lefty polypeptides are described, for example, in U.S. Pat. No. 8,106,004, herein incorporated by reference in its entirety. As used herein, the terms "Lefty A/B" and "Lefty" are interchangeable and refer to either Lefty A or Lefty B, or both Lefty A and Lefty B in combination. In some embodiments, Lefty is isolated from a microenvironment (e.g., an environment that comprises a basement membrane or other defined matrix that is in contact with embryonic stem cells, such as human embryonic stem cells (hESCs)). In one embodiment, Lefty, isolated from a microenvironment, may be substantially pure. In another embodiment, Lefty may be present in combination with other hESC factors. As used herein, by "substantially pure" it is meant a preparation which is at least 70% by weight (dry weight) the compound of interest, e.g., hESC-derived Lefty. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

In another embodiment, the invention provides an isolated Lefty protein produced by conditioning a matrix with human embryonic stem cells. As used herein, "conditioning a matrix" refers to preparing a preconditioned microenvironment as defined herein. In certain embodiments, the matrix is conditioned with hESCs from 0 to 10 days or any range in between, including, but not limited to, from 0.5 to 10 days, from 2 to 8 days, from 3 to 6 days, from 3 to 5 days, from 3 to 4 days, or for 1, 2, 3, 4, or 5 days. Lefty may be isolated from the matrix by any method known to one of skill in the art, including through use of anti-Lefty antibodies.

In one embodiment, the invention provides a protein comprising glycosylated Lefty. In this embodiment, Lefty may be glycosylated to varying degrees, and may comprise one or more N- and/or O-linked glycosylation sites, or a combination thereof. In one embodiment, the glycosylated Lefty is characterized in that more than 0%, 5%, 10%, 15%, 20%, 25%, 30%, 35%, 40%, 45%, 50%, 55%, 60%, 65%, 70%, 75%, 80%, 85%, 90%, or 95% of the possible N- and/or O-glycosylation sites are glycosylated. In another embodiment, the glycosylated Lefty is characterized in that less than 100%, 95%, 90%, 85%, 80%, 75%, 70%, 65%, 60%, 55%, 50%, 45%, 40%, 35%, 30%, 25%, 20%, 15%, 10%, or 5% of the possible N- and/or O-glycosylation sites are glycosylated. In another embodiment, the glycosylated Lefty is characterized in that the percentage of possible N- and/or O-glycosylation sites that are glycosylated is based on a combination of the "more than" and "less than" percentages recited above. Thus, in one non-limiting example, the glycosylated Lefty is characterized in that more than 30% and less than 70% of the possible N- and/or O-glycosylation sites are glycosylated. In another embodiment, 100% of the possible N- and/or O-glycosylation sites are glycosylated.

In one embodiment, the glycosylated Lefty is glycosylated to substantially the same extent as Lefty derived from hESCs.

Glycosylated Lefty may be prepared by any method, including by recombinant methods (see, e.g. Sambrook et al., 2001, Molecular Cloning: A Laboratory Manual, 3rd ed., Cold Spring Harbor Laboratory Press, Cold Spring Harbor, N.Y.). In one embodiment, glycosylated Lefty is prepared recombinantly in Chinese Hamster Ovary (CHO) or human embryonic kidney (HEK) cells. Alternatively, glycosylated Lefty may be prepared by chemical synthesis methods (such as solid phase peptide synthesis) using techniques known in the art such as those set forth by Merrifield et al., 1963, J. Am. Chem. Soc. 85:2149; Houghten et al., 1985, Proc Natl Acad. Sci. USA 82:5132; and Stewart and Young, Solid Phase Peptide Synthesis (Pierce Chemical Co. 1984), or by a combination of synthetic and recombinant techniques. Glycosylated Lefty may also be prepared by isolation from hESCs, including by isolation from the microenvironment of hESCs.

Included within the scope of the invention are fragments or derivatives of Lefty or glycosylated Lefty. As used herein, "fragment" means any portion of the full length Lefty sequence having an activity of the full length protein, including, but not limited to, the ability to inhibit Nodal. Included in the scope of "fragments" are naturally occurring enzymatic cleavage products. Included in the scope of the term "derivatives" are derivatives of full length Lefty as well as fragments thereof. As used herein, "derivative" or "derivatives" includes variations of Lefty having one or more amino acid residues which have been added, deleted, inserted or substituted, where the resulting polypeptide has an activity of Lefty, including, but not limited to, the ability to inhibit Nodal. As used herein, "derivatives" also includes chemical derivatives of Lefty and variations thereof. It will be understood to one of skill in the art that these variations may occur in any combination.

In some embodiments the Lefty compositions comprise a Lefty peptide mimetic (peptidomimetic). The use of peptides as lead compounds, and subsequently conversion into low-molecular-weight nonpeptide molecules (peptidomimetics), has led to development of small-molecule antagonists of intracellular targets (Bottger et al., J Mol Biol, 1997. 269(5): p. 744-56; Bottger et al., Oncogene, 1996. 13(10): p. 2141-7). Therefore, peptidomimetics have emerged as a powerful means for overcoming the limitations inherent in the physical characteristics of peptides, improving their therapeutic potential (Kieber-Emmons et al., Curr Opin Biotechnol, 1997. 8(4): p. 435-41; Beeley, Trends Biotechnol, 1994. 12(6): p. 213-6; Moore et al., Trends Pharmacol Sci, 1994. 15(4): p. 124-9). In some embodiments, compared to native peptides, peptidomimetics possess desirable pharmacodynamic properties superior to natural peptides, including good oral activity, long duration of action, better transport through cellular membranes, decreased rate of excretion, and decreased hydrolysis by peptidases.

Development of a small molecule peptidomimetic generally involves identification of the smallest functional peptide unit capable of inhibiting the targeted interaction. A growing body of literature demonstrates that high-affinity ligands can be selected from peptide libraries displayed on bacteriophages (Sulochana and Ge, Curr Pharm Des, 2007. 13(20): p. 2074-86; Cwirla et al., Proc Natl Acad Sci USA, 1990. 87(16): p. 6378-82; Scott and Smith, Science, 1990. 249 (4967): p. 386-90; Devlin et al., Science, 1990. 249(4967): p. 404-6), and many applications have been directed toward antagonizing the function of a protein ligand (Dower, Curr Opin Chem Biol, 1998. 2(3): p. 328-34; Sidhu et al., Methods Enzymol, 2000. 328: p. 333-63). Because the libraries can be very large ($10^{11}$ or more individual members), no initial assumptions are required concerning how to bias the library, nor the selective enrichment of rare binding phage through biological amplification and rescreening. Those sequences that bind can be identified by sequencing their encoding DNA.

Chemically modified derivatives of glycosylated Lefty may be prepared by one skilled in the art, in view of the disclosures described herein. Glycosylated Lefty derivatives are modified in a manner that is different—either in the type or location of the molecules naturally attached to the polypeptide. Derivatives may include molecules formed by the deletion of one or more naturally-attached chemical group, or they may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules which may be used to prepare covalently attached glycosylated Lefty polypeptide multimers.

In general, chemical derivatization may be performed under any suitable condition used to react a protein with an activated polymer molecule. The optimal reaction conditions will be determined based on known parameters and the desired result. For example, the larger the ratio of polymer molecules to protein, the greater the percentage of attached polymer molecule. In one embodiment, the glycosylated Lefty derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, Focus on Growth Factors 3:4-10; European Patent Nos. 0154316 and 0401384; and U.S. Pat. No. 4,179,337.

In another embodiment, glycosylated Lefty polypeptides may be chemically coupled to biotin. The biotin/glycosylated Lefty polypeptide molecules are then allowed to bind to avidin, resulting in tetravalent avidin/biotin/glycosylated Lefty polypeptide molecules. Glycosylated Lefty polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present glycosylated Lefty derivatives include those described herein for glycosylated Lefty. However, the glycosylated Lefty derivatives disclosed herein may have additional activities, enhanced or reduced biological activity, or other characteristics, such as increased or decreased half-life, as compared to the non-derivatized molecules.

B. Compositions for Topical Application

In some embodiments, the present invention provides compositions comprising Lefty that are formulated for topical administration. In some embodiments, pharmaceutical compositions comprise an effective amount of one or a plurality of Nodal inhibitors together with a pharmaceutically acceptable diluent, carrier, solubilizer, emulsifier, preservative and/or adjuvant, wherein the pharmaceutical composition is capable of inducing a desired therapeutic effect when properly administered to a patient. Preferably, acceptable formulation materials are nontoxic to recipients at the dosages and concentrations employed.

In some embodiments, topical formulations are formulated to prevent degradations of Lefty and allow the polypeptide to enter skin cells. In some embodiments, topical formulations comprise one or more of the following components: histamine dihydrochloride, ethanol, trolamine, carbomer (e.g., Carbopol 974P), methyl paraben, propyl paraben, Lefty (e.g., rhLefty), and PBS. In some embodiments, compositions for topical administration are aqueous and do not include any waxy components. In some embodiments, compositions are formulated as liposomal formulations. In some embodiments, topical compositions are formulated for spray or aerosol applications.

In some embodiments, topical formulations for ophthalmic use are formulated (e.g., as saline drops).

In some embodiments, compositions comprise Lefty (e.g., a glycosylated Lefty) at a dosage between 0.01 and 500 ng/mL, between 0.01 and 200 ng/mL, between 0.1 and 200 ng/mL, between 0.1 and 100 ng/mL, between 1 and 100 ng/mL, between 10 and 100 ng/mL, between 10 and 75 ng/mL, between 20 and 75 ng/mL, between 20 and 50 ng/mL, between 25 and 50 ng/mL, or between 30 and 40 ng/mL.

In certain embodiments, a pharmaceutical composition useful in the methods of the invention may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See REMINGTON'S PHARMACEUTICAL SCIENCES, 18.sup.th Edition, (A. R. Gennaro, ed.), 1990, Mack Publishing Company.

In certain embodiments, the optimal pharmaceutical compositions are determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of release and rate of clearance of the Lefty.

In certain embodiments, the primary vehicle or carrier in a pharmaceutical composition may be either aqueous or non-aqueous in nature. For example, a suitable vehicle or carrier may be water, possibly supplemented with other materials common in compositions for topical administration.

Alternatively, it is possible to entrap the therapeutic agents, for delivery, in microcapsules prepared, for example, by coacervation techniques or by interfacial polymerization, for example, by the use of hydroxymethyl cellulose or gelatin-microcapsules or poly(methylmethacrylate) microcapsules, respectively, or in a colloid drug delivery system, for example, liposomes, albumin, microspheres, microemulsions, nanoparticles, nanocapsules, or in macroemulsions. Such teachings are disclosed in Remington's Pharmaceutical Sciences (1980), herein incorporated by reference.

The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. All transdermal delivery systems are contemplated herein, including, but not limited to, single-layer drug-in-adhesives, multi-layer drug-in-adhesives, reservoirs, matrixes, vapour patches, wafers (e.g., lyophilized wafers), systems employing iontophoresis, non-cavitational ultrasound, electroporation, cavitational ultrasound, microneedles, thermal ablation, microdermabrasion, and the like.

II. Uses of Topical Lefty Formulations

Embodiments of the present disclosure provide topical Lefty compositions for treating and preventing disease on body surfaces or mucosal layers. In some embodiments, topical Lefty formulations find use for application to any tissue of ectodermal original (e.g., skin, mucosal surfaces, cornea, neural crest origin tissue (e.g., melanocytes, retina, etc.), etc.). The present disclosure is not limited to a particular cancer. Topical Lefty formulations find use in the treatment of variety of cancers and precancerous conditions. Examples include, but are not limited to, skin cancer (e.g., basal cell carcinoma (BCC), squamous cell carcinoma (SCC) and malignant melanoma), extodermal dysplasia, and other cancers of body or mucosal (e.g., buccal mucosa, esophageal mucosa, gastric mucosa, intestinal mucosa. nasal mucosa, olfactory mucosa, oral mucosa, bronchial mucosa, endometrium, or penile mucosa).

In some embodiments, topical Lefty compositions are used to treat cancers. For example, in some embodiments, a topical Lefty composition is applied to a cancerous lesion. In some embodiments, a topical Lefty composition is applied to a removal site after surgical or other removal of a cancerous lesion.

In some embodiments, topical Lefty compositions are used to treat pre-cancerous conditions or prevent pre-cancerous lesions from progressing to cancers. For example, in some embodiments, a topical Lefty composition is applied to a pre-cancerous lesion. In some embodiments, a topical Lefty composition is applied to a removal site after surgical or other removal of a pre-cancerous lesion.

In some embodiments, the cancerous or pre-cancerous lesion is a nevi. For example, in some embodiments, nevi suspected of being cancerous or pre-cancerous or diagnosed as cancerous or pre-cancerous are treated with a topical Lefty composition. In some embodiments, the removal site of a nevi is treated with a topical Lefty composition after the nevi is removed.

In some embodiments, the nevi or subjects identified or suspected of having a high risk of developing cancerous nevi are prophylactically treated with a topical Lefty composition.

The present disclosed is not limited to the treatment and prevention of cancer. In some embodiments, topical Lefty compositions find use the treatment of artificial skin or skin transplants derived from stem cells. In such embodiments, the topical Lefty compositions prevent further differentiation of the skin cells (e.g., to control modeling and architecture).

In some embodiments, topical Lefty compositions are applied to the eye. In some embodiments of such ophthalmic applications, the Lefty formulation is typically in a saline drop form. In some embodiments, topical Lefty compositions are used to treat disorders of the eye mucosal membranes such as cancers and other diseases.

In some embodiments, topical Lefty compositions are used to treat cancer stem cells (e.g., by preventing differentiation into cancers).

In some embodiments, treatment with topical Lefty compositions is administered one or more times to a given location (e.g., one or more times a day for a period of days, weeks, or months). In some embodiments, treatment is long term or ongoing (e.g., administered one or more times per day for a period of weeks, months, or years).

Administration may be conducted by any suitable method, including, but not limited to, application of a transdermal device, irrigation of a lesion location or site of removal of a lesion, spray delivery, droplet delivery, nebulizer delivery, pump delivery, powder delivery, gel delivery, and the like.

III. Combination Therapy

In some embodiments, the present invention provides therapeutic methods comprising one or more compositions described herein in combination with an additional agent (e.g., a chemotherapeutic agent). The present invention is not limited to a particular chemotherapy agent.

In some embodiments, a topical Lefty composition is administered concurrently with an additional agent (e.g., chemotherapy agent). In some embodiments, a topical Lefty composition and an additional agent are administered sequentially. For example, in some embodiments, a topical Lefty composition is administered following an additional agent. In some embodiments, there is a gap (e.g., 1, 2, 3, 4, 5, 6, 7, 8, 9, 10 or more day or several weeks or months) in between administration of the topical Lefty composition and the additional agent.

Various classes of antineoplastic (e.g., anticancer) agents are contemplated for use in certain embodiments of the present invention. Anticancer agents suitable for use with embodiments of the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of embodiments of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent that is routinely used in a cancer therapy context finds use in the compositions and methods of embodiments of the present invention. For example, the U.S. Food and Drug Administration maintains a formulary of oncolytic agents approved for use in the United States. International counterpart agencies to the U.S. F.D.A. maintain similar formularies. The below Table provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |

| | | |
|---|---|---|
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile,a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-l-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |

| | | |
|---|---|---|
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3, 17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |

| | | |
|---|---|---|
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4': 6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((—)-(S)-2,3,5,6-tetrahydro-6-phenylimidazo [2,1-b] thiazole monohydrochloride $C_{11}H_{12}N_2S$•HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |

| | | |
|---|---|---|
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11 - 17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |

| | | |
|---|---|---|
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| Teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Where methods and compositions of the present invention are used for treatment or prevention of cancer, existing therapies for the treatment of cancer (e.g., melanoma) may be used in combination with the present methods.

Experimental

The following examples are provided in order to demonstrate and further illustrate certain preferred embodiments and aspects of the present invention and are not to be construed as limiting the scope thereof.

Moles, also referred to as nevi, consist of melanocytes that have become activated or transformed to proliferate and form a mass on the skin. Moles are classified as benign or dysplastic or a status between the two states. Dysplastic moles can contain Nodal-positive melanocytes. Because Nodal is associated with cancer stem cells, inhibition of Nodal expression in melanocytes by Lefty was investigated. Lefty was applied to skin to neutralize Nodal expression and render the melanocytes nonproliferative. Lefty is delivered using various delivery systems.

Similarly, other ectodermal dysplasia or carcinomas are considered the most common form(s) of cancer, which also express Nodal. Therefore, Lefty is also applied to these lesions before or after removal to maintain homeostasis and prevent or treat cancer.

Materials and Methods:
 Emollient A
 Histamine dihydrochloride (0.9 mg)
 Ethanol, USP (200 proof) (17.6 mg)
 Trolamine, NF (9.0 mg)
 Carbomer, NF (Carbopol 974P) (8.0 mg)
 Methyl Paraben, NF (2.0 mg)
 Propyl Paraben, NF (0.2 mg)
 rhLefty (10 ng, 50 ng, 100 ng, 500 ng/ml)
 PBS, USP Qs
 Control
 rhLefty (10 ng, 50 ng, 100 ng, 500 ng/ml)
 PBS, USP Human transformed melanocytes, transfected non-aggressive melanoma cells and squamous cell carcinoma cells were treated with varying concentrations of rhLefty (10 ng-500 ng/ml) suspended in Emollient A or only PBS (as a control) over 48 hours in vitro. Subsequently, cells were lysed and prepared for Western Blot analysis, specifically to measure Nodal expression. Separately, rhLefty suspended in Emollient A, and rhLefty suspended in PBS, were assessed by Western Blot analysis to determine Lefty's protein integrity.

Results: Nodal expression in human transformed melanocytes, transfected non-aggressive melanoma cells, and squamous cell carcinoma cells was down-regulated in a dose dependent manner in both rhLefty/Emollient A and the rhLefty/Control. Western Blot analysis of rhLefty/Emollient A further revealed three bands (@42 KDa, @34 KDa, @28 KDa) indicative of hLefty, indicating that Lefty protein is not adversely affected nor degraded by Emollient A.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

I claim:

1. A pharmaceutical composition comprising isolated Lefty, ethanol, trolamine, carbomer, methyl paraben, propyl paraben, and phosphate buffered saline (PBS); wherein said composition is formulated as a gel for topical administration.

2. The composition of claim 1, wherein said Lefty is a peptide.

3. The composition of claim 1, wherein said Lefty is glycosylated.

4. The composition of claim 3, wherein said Lefty is recombinant human Lefty.

5. The composition of claim 3, wherein said Lefty is isolated from human embryonic stem cells.

6. The composition of claim 1, wherein said composition further comprises histamine.

7. The composition of claim 1, wherein said Lefty is present in said composition as a concentration of between 1 ng/ml and 1000 ng/ml.

8. A pharmaceutical composition comprising isolated Lefty, ethanol, trolamine, carbomer, methyl paraben, propyl paraben, and phosphate buffered saline (PBS); wherein said composition is formulated as a transdermal device for topical administration.

* * * * *